United States Patent
Roso et al.

(10) Patent No.: US 7,651,691 B2
(45) Date of Patent: Jan. 26, 2010

(54) EMULSIFYING COMPOSITIONS BASED ON FATTY ALCOHOL AND ALKYLPOLYGLYCOSIDES

(75) Inventors: Alicia Roso, Saix (FR); Chantal Amalric, Blan (FR); Nelly Michel, Maisons Alfort (FR); Jean-Pierre Boiteux, Saix (FR); Guy Tabacchi, Paris (FR); Alain Milius, Nice (FR)

(73) Assignee: Societe d'Exploitation de Produite pour les Industries Chimiques SEPPIC, Paris (FR)

( * ) Notice: Subject to any disclaimer, the term of this patent is extended or adjusted under 35 U.S.C. 154(b) by 0 days.

(21) Appl. No.: 10/492,394

(22) PCT Filed: Oct. 2, 2002

(86) PCT No.: PCT/FR02/03352

§ 371 (c)(1),
(2), (4) Date: Nov. 12, 2004

(87) PCT Pub. No.: WO03/030838

PCT Pub. Date: Apr. 17, 2003

(65) Prior Publication Data

US 2005/0069512 A1   Mar. 31, 2005

(30) Foreign Application Priority Data

Oct. 11, 2001 (FR) .................... 01 13088

(51) Int. Cl.
*A61K 9/00* (2006.01)
*A61K 8/02* (2006.01)
(52) U.S. Cl. ...................... 424/400; 424/401
(58) Field of Classification Search .......... 424/400–401
See application file for complete search history.

(56) References Cited

U.S. PATENT DOCUMENTS 4,917,883 A * 4/1990 Strobridge .................. 424/59
5,670,471 A * 9/1997 Amalric et al. ............. 510/416
5,868,826 A   2/1999 Fischer et al.
5,958,431 A * 9/1999 Brancq et al. ............... 424/401
6,066,753 A * 5/2000 Turowski-Wanke et al. . 558/208
6,335,025 B1* 1/2002 Lorant ........................ 424/401
6,353,034 B1* 3/2002 Amalric et al. ............... 516/72
6,541,016 B1* 4/2003 Turowski-Wanke et al. . 424/401

FOREIGN PATENT DOCUMENTS

| FR | 96 14283 | 11/1996 |
|---|---|---|
| FR | 97 04876 | 4/1997 |
| FR | 2 762 317 | 10/1998 |
| WO | WO 97/46219 | 12/1997 |
| WO | WO 99/13830 | 3/1999 |
| WO | WO 99/59537 | 11/1999 |
| WO | WO 01/41896 | 6/2001 |

OTHER PUBLICATIONS

International Search Report for PCT/FR02/03352.
Patent Abstracts of Japan; publication No. 62148419; publication date Jul. 23, 1987; application date Dec. 23, 1985; application No. 60291078.
"O/W emulsions for cosmetics products stabilized by alkyl phosphates—rheology and storage tests"; D. Miller, E. Wiener, A. Turowski, C. Thunig, H. Hoffman; XP-002230451; received Feb. 3, 1998, accepted Jul. 7, 1998.
Polo et al. in DCI (Sep. 1989), pp. 26-34 and 82-84.

* cited by examiner

*Primary Examiner*—Sreeni Padmanabhan
*Assistant Examiner*—Renee Claytor
(74) *Attorney, Agent, or Firm*—Young & Thompson

(57) ABSTRACT

An emulsifying composition and process, that includes:
a) from about 10 to about 90% by weight of arachidyl or behenyl alcohol;
b) from about 10 to about 90% by weight of the corresponding phosphoric ester of arachidyl or behenyl alcohol; and
c) up to about 20% by weight of at least one alkylpolyglycoside.

29 Claims, No Drawings

EMULSIFYING COMPOSITIONS BASED ON FATTY ALCOHOL AND ALKYLPOLYGLYCOSIDES

BACKGROUD OF THE INVENTION

1. Field of the Invention

A subject matter of the present invention is specific emulsifying compositions which find application in particular in the cosmetics field.

2. Related Art

Phosphoric esters of fatty alcohols, in particular alkyl phosphates prepared from a fatty alcohol having from 14 to 18 carbon atoms, are known as being emulsifiers. The use of cetyl phosphates as emulsifiers in cosmetics is reported by Polo et al. in DCI (September 1999), 26-34 and 82-84.

Cosmetic formulators are continually searching for novel emulsion feels which do not exhibit the disadvantage of being rich. Patent application FR-A-2 762 317 discloses in particular $C_{20-22}$ alkylpolyglycosides+$C_{20-22}$ alcohol combinations which result in emulsions which are not very greasy and evanescent but which are still considered to be too greasy for some skin types. One of the problems to be solved thus consists in having available emulsions which exhibit a better cosmetic feel than that of conventional emulsions while combining rapid penetration, a light and nongreasy feel and a sensation of freshness.

Emulsions with an aqueous continuous phase are known for their low resistance to water and the formulator attempts to overcome this defect by combining, with his emulsifying system, additives such as hydrophobic polymers (Antaron, Ganex, Dermacryl LT79, Glossamer) and/or coemulsifiers, in particular cetyl phosphates, such as those of the Amphisol range. These additives leave a significant residual film on the skin. Another problem consists in having available emulsions which exhibit better resistance to water in combination with the absence of a sensation of a residue.

Makeup emulsions (foundation, mascaras, cream eyeshadow) with an aqueous continuous phase are predominantly formulated based on stearic acid or on a stearic acid derivative (PEG stearate, glyceryl stearate). The stabilization of the inorganic fillers in these emulsions is a critical point: the tendency is to obtain reagglomeration of the pigments over time, which compromises the smooth and uniform texture (specks on application or else migration of the pigments within the product with the appearance of colored streaks). The stabilizing systems of the aqueous phase, in combination with the emulsifying system, are therefore sophisticated and include, most of the time, the presence of at least two polymers (of synthetic or natural origin). Furthermore, these emulsions with an aqueous continuous phase have the disadvantage of exhibiting, on the skin, significant phenomena of migration during the day. Finally, because of the nature and the performance of the emulsifiers used, these emulsions with an aqueous continuous phase are generally found formulated at a pH in the region of 7, i.e. a pH markedly higher than the average skin pH (5.5).

Another problem consists in having available emulsions which exhibit a better hold of the makeup.

Another problem consists in formulating emulsions in which the fillers and/or pigments possibly present are stabilized in an easy and lasting manner with the minimum amount of stabilizers in the aqueous phase.

Another problem consists in formulating makeup emulsions comprising pigments, in particular titanium dioxide, at a pH in the region of the average skin pH, in particular of between 5 and 6.

It has now been discovered unexpectedly, and this is the basis of the invention, that the combination of an alcohol having 20 or 22 carbon atoms and of a phosphated alcohol having 20 or 22 carbon atoms makes it possible (i) to obtain emulsions with an improved feel, (ii) to improve the resistance of the emulsions to water, and (iii) to improve makeup emulsions.

SUMMARY OF THE INVENTION

This invention provides an emulsifying composition and process, that comprises:

a) from about 10 to about 90% by weight at least one alcohol, wherein said alcohol is selected from the group consisting of arachidyl alcohol and behenyl alcohol;

b) from about 10 to about 90% by weight at least one phosphoric ester of said at least one alcohol; and c) up to about 20% by weight at least one alkylpolyglycoside represented by the formula:

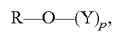

$$R\text{—}O\text{—}(Y)_p,$$

wherein said R represents an alkyl radical having from about 14 to about 22 carbon atoms;

wherein said Y represents the residue of a $C_5$ or $C_6$ monosaccharide; and wherein said p is the average degree of polymerization, and represents a decimal number in the range of from about 1 to about 5.

DESCRIPTION OF PREFERRED EMBODIMENTS

Thus, according to a first aspect, a subject matter of the invention is an emulsifying composition comprising:

10 to 90% by weight, preferably 15 to 90% by weight and more preferably 30 to 70% by weight of arachidyl alcohol and/or of behenyl alcohol; and 90 to 10% by weight, preferably 85 to 10% by weight and more preferably 70 to 30% by weight of phosphoric ester of arachidyl alcohol and/or of phosphoric ester of behenyl alcohol (hereinafter also denoted by "phosphated alcohol(s)").

The term "phosphoric ester of arachidyl and/or behenyl alcohol" is understood to mean a monoester, a diester, a triester or a mixture in all proportions of mono-, di- and triester of the alcohol concerned.

According to a specific embodiment, the mixture of alcohol(s) and of phosphated alcohol(s) can additionally comprise up to 20% by weight, preferably from 1 to 10% by weight, of one or more alkylpolyglycosides of formula R—O—(Y)$_p$ in which R represents an alkyl radical having from 14 to 22 carbon atoms, preferably from 20 to 22 carbon atoms, Y represents the residue of a $C_5$ or $C_6$ monosaccharide, preferably of a glucose or of a xylose, and p represents a decimal number within the range from 1 to 5, preferably within the range from 1 to 2.5 and particularly preferably within the range from 1 to 2.

In the formula R—O—(Y)$_p$, the R—O— group is bonded to Y via the anomeric carbon of the glucose or xylose residue, so as to form an acetal functional group.

When the emulsifying composition according to the invention comprises one or more alkylpolyglycosides, it can be prepared either conventionally, by mixing the various constituents, or, in a more novel way, by a process which involves a one-pot reaction.

Thus, according to a second aspect, a subject matter of the invention is a process for the preparation of such an emulsifying composition which comprises:
(i) the phosphation of the alcohol or alcohols; and
(ii) the reaction of the unreacted alcohol or alcohols with a reducing sugar ($C_5$ or $C_6$ monosaccharide), such as glucose or xylose.

The second stage of the process is generally carried out in the presence of strong acid catalysts, such as, for example, sulfuric acid.

This process is very easy to carry out since the two stages described above are carried out in the same industrial unit.

The composition according to the invention makes it possible to very readily formulate emulsions, in particular makeup emulsions and antisun emulsions.

Thus, according to a third aspect, a subject matter of the invention is the use of the composition described above as emulsifying agent for the preparation of emulsions.

According to a fourth aspect, another subject matter of the invention is an emulsion comprising the emulsifying composition described above. This composition generally represents from 0.2 to 10% by weight of the emulsion.

The emulsion also comprises from 1 to 50% by weight, preferably from 5 to 35% by weight and more preferably from 5 to 25% by weight of a fatty phase composed of one or more oils and/or of one or more waxes.

The oil is advantageously chosen from the following oils:
oils of vegetable origin, such as sweet almond oil, coconut oil, castor oil, jojoba oil, olive oil, rapeseed oil, groundnut oil, sunflower oil, wheat germ oil, corn germ oil, soybean oil, cottonseed oil, alfalfa oil, poppy oil, pumpkinseed oil, evening primrose oil, millet oil, barley oil, rye oil, safflower oil, candlenut oil, passionflower oil, hazelnut oil, palm oil, karite butter, apricot kernel oil, calophyllum oil, sisymbrium oil, avocado oil or calendula oil;
vegetable oils and their methyl esters which are ethoxylated;
oils of animal origin, such as squalene or squalane;
mineral oils, such as liquid paraffin, liquid petrolatum and isoparaffins;
synthetic oils, in particular fatty acid esters, such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, or fatty acid monoglycerides, diglycerides and triglycerides, such as glyceryl triheptanoate, alkyl benzoates, poly-α-olefins, polyolefins, such as polyisobutene, synthetic isoalkanes, such as isohexadecane or isododecane, perfluorinated oils and silicone oils.

This oil can also be chosen from fatty acids, fatty alcohols, waxes of natural or synthetic origin and more generally still any fatty substance of vegetable, animal or synthetic origin.

The wax is advantageously chosen from fatty substances which are solid at ambient temperature, such as, for example, beeswax; carnauba wax; candelilla wax; ouricury wax; Japan wax; cork fiber or sugarcane wax; paraffin waxes; lignite waxes; microcrystalline waxes; lanolin wax; ozokerite; polyethylene wax; hydrogenated oils; silicone waxes; vegetable waxes; fatty alcohols and fatty acids which are solid at ambient temperature; or glycerides which are solid at ambient temperature.

The emulsion in accordance with the invention can also comprise up to 10% by weight of stabilizing agent, such as, for example, magnesium silicate; aluminum silicate; sodium silicate; xanthan gum; acacia gum; locust bean gum; scleroglucan gum; gellan gum; alginates; cellulose and cellulose derivatives; clays; starches and starch derivatives; acrylic acid polymers and copolymers; acryloyldimethyl taurate polymers and copolymers; polyvinylpyrrolidone; acrylamide polymers and copolymers; or polyurethanes.

Generally, the emulsion in accordance with the invention can also comprise up to 10% by weight of one or more additives generally used in cosmetics and chosen from:
coemulsifiers, such as, for example, fatty acids; ethoxylated fatty acids; esters of fatty acids and of sorbitol; ethoxylated fatty acid esters; polysorbates; polyglycerol esters; ethoxylated fatty alcohols; sucrose esters; alkylpolyglycosides; or sulfated and phosphated fatty alcohols;
dispersants conventionally used in cosmetics, in particular lauryl sulfate; lauryl ether sulfate; octenyl-sulfosuccinate; lauryl sarcosinate; dimethicone copolyol phosphate, such as, for example, the product sold under the name Pecosil® PS100; acrylic polymers and copolymers, such as, for example, those sold under the name Avalure®; or lauroylamino acids, such as, for example, the product sold under the name Proteol OAT®;
preservatives generally used in cosmetics;
fragrances or other additives with a scenting function (such as, in particular, essential oils and essential waxes);
DHA; antiwrinkle active agents, moisturizing active agents, soothing active agents, active agents for combating free radicals, antioxidizing active agents or seboregulating active agents; inorganic salts; vitamins; phytosterols; polyphenols; or sphingolipids.

According to an advantageous embodiment, the emulsion in accordance with the invention is a makeup emulsion. In this specific scenario, the emulsion comprises from 0.5 to 50% by weight, preferably from 2 to 35% by weight, of organic or inorganic pigments and/or fillers.

These pigments and/or fillers can be lamellar or spherical and without specific limitation with regard to their particle size. Mention may be made, by way of example, in particular of poly(methyl methacrylate); crosslinked methacrylic acid copolymers; nylon; poly(β-alanine); polyethylene; Teflon; lauroyllysine; alkylamino acid, starch or PTFE powders; hollow microspheres, such as, for example, those sold under the name Expancel® or Polytrap®; silicone resin microbeads; titanium dioxide; zinc oxide; (black, red or yellow) iron oxide; iron titanate; carbon black; chromium oxide; chromium hydroxide; zirconium oxide; cerium oxide; cobalt titanate; ultramarine; prussian blue; titanium oxide-coated mica; bismuth oxychloride; pearl essence; talc; aluminum powder; copper powder; gold powder; mica; sericite; kaolin; phlogopite; synthetic mica; lepidolite; biotite; vermiculite; calcium carbonate; magnesium carbonate and magnesium hydroxycarbonate; aluminum silicate; barium silicate; calcium silicate; magnesium silicate; strontium silicate; silica and silica microspheres; ceramic and glass microspheres; zeolites; hydroxyapatite; metal salts of tungstic acid; barium sulfate; gypsum; calcium phosphate; metal soaps of fatty acids; boron nitride; photochromic pigments; or interferential pigments. These fillers may have been subjected to a surface treatment.

The makeup emulsion according to the invention can also comprise up to 20% by weight, preferably up to 10% by weight, of one or more cosolvents, such as, for example, glycerol; sorbitol; PEG; monopropylene glycol; butylene glycol; isoprene glycol; 2-methyl-1,3-propanediol; ethanol; or hexylene glycol.

According to another advantageous embodiment, the emulsion in accordance with the invention is an antisun emulsion. In this specific scenario, the emulsion comprises from 1 to 40% by weight, preferably from 1 to 20% by weight, of one or more organic or inorganic sunscreens; and up to 30% by weight, preferably up to 10% by weight, of a water-resisting agent.

The emulsion in accordance with the invention can also comprise a sufficient amount of base, such as, for example, sodium hydroxide, potassium hydroxide, ammonia, triethanolamine, tetrahydroxypropylethylenediamine, tris-hydroxyaminomethane or aminomethylpropanol, in order to adjust the final pH of the emulsion to between 3 and 10.

Very clearly, the sum of the various constituents of the emulsion according to the invention is equal to 100%.

The emulsions in accordance with the invention can be prepared according to the procedure described below.

The aqueous phase, optionally comprising the cosolvent(s) and the base, is heated to a temperature of 70 to 85° C. This aqueous phase comprises, if appropriate, the fillers and/or the pigments, which can be milled beforehand; the stabilizing agents; the dispersants; and the preservatives, fragrances and other active agents.

At the same time, the fatty phase, comprising the emulsifying composition, the oils and/or the waxes, is heated to an identical temperature of 70 to 85° C.

The two phases are subsequently mixed and emulsified using a device of rotor-stator type (Silverson laboratory mixer or Olsa, Rayneri or Becomix industrial devices). After emulsifying for a few minutes, the emulsion is cooled with moderate stirring.

EXAMPLES

The invention is illustrated using the following examples.

Example 1

Synthesis of an Emulsifier According to the Invention 50 kg of alcohol (mixture of $C_{20}$ and $C_{22}$ alcohols in a 70/30 ratio) are introduced into a reactor preheated to 70° C. under gentle nitrogen sparging. Once the mixture of alcohols has melted, 3.88 kg of phosphorus pentoxide are gradually added. The reaction medium is maintained at 85° C. for 4 h 30 and is then discharged.

The product obtained has the following characteristics:

| | |
|---|---|
| appearance | white solid |
| acid number | 90.4 mg KOH/g |
| $C_{20}$-$C_{22}$ alcohol | 46.0% |
| phosphated $C_{20}$-$C_{22}$ alcohol | 54.0% |

Example 2

Synthesis of an Emulsifier According to the Invention 24.3 kg of the product obtained according to example 1 are reacted at 110° C. with 1.13 kg of anhydrous glucose in the catalytic presence of sulfuric acid for 8 hours. The product obtained after filtration exhibits the following characteristics:

| | |
|---|---|
| appearance | white solid |
| $C_{20}$-$C_{22}$ alcohol | 43% |
| phosphated $C_{20}$-$C_{22}$ alcohol | 54% |
| $C_{20}$-$C_{22}$ alkylpolyglucoside | 3% |

To demonstrate the invention, the emulsifiers tested are shown in table 1. The emulsifiers C and G are emulsifiers according to the invention. The others are by way of comparison.

TABLE 1

| | EMULSIFIER |
|---|---|
| A | Phosphated $C_{16}$ alcohol + $C_{16-18}$ alcohol (50/50) |
| B | Phosphated $C_{16}$ alcohol + $C_{20-22}$ alcohol (50/50) |
| C (ex. 1) | Phosphated $C_{20-22}$ alcohol + $C_{20-22}$ alcohol (54/46) |
| D | $C_{20-22}$ alkylpolyglucoside + $C_{20-22}$ alcohol (20/80) |
| E | Phosphated $C_{20-22}$ alcohol |
| F | Phosphated $C_{20-22}$ alcohol + $C_{16-18}$ alcohol (50/50) |
| G (ex. 2) | Phosphated $C_{20-22}$ alcohol + $C_{20-22}$ alcohol + $C_{20-22}$ alkylpolyglucoside (54/43/3) |
| H | Stearic acid + PEG 100 stearate (67/33) |

The phosphated $C_{16}$ alcohol is sold by Givaudan-Roure under the name Amphisol® A.

The $C_{20-22}$ alcohols and the $C_{16-18}$ alcohols are 70/30 and 50/50 mixtures respectively.

The phosphated $C_{20-22}$ alcohol is prepared under the conditions of example 1, using 0.75 kg of $C_{20-22}$ alcohol and 0.22 kg of phosphorus pentoxide.

Example 3

Demonstration of the Improvement in Feel

Emulsions are prepared which have the following composition:

| | |
|---|---|
| Fatty phase | |
| Emulsifier | 5% |
| Cetearyl octanoate | 15% |
| Aqueous phase | |
| Water | q.s. for 100% |
| Tromethamine | q.s. pH = 5.5 |
| Preservatives | q.s. |

The emulsions prepared are monitored by a sensory evaluation: the criteria of comfort are graded from 0 to 5 by a jury of experts after application to the face. The following are evaluated: the feeling of greasiness (0=nongreasy and 5=very greasy) and the presence of residue (0=absence of residue and 5=significant residue).

The results are presented in table 2.

TABLE 2

| Emulsifier | A | B | C | D | E | F |
|---|---|---|---|---|---|---|
| Sensory evaluation: | | | | | | |
| greasiness | 3 | 3 | 0 | 2 | — | 3 |
| residue | 4 | 2 | 0 | 1 | — | 4 |

The emulsifier according to the invention is distinguished by its nongreasy feel and by the absence of residue on the skin. It should be noted that the emulsion E is not stable.

Example 4

Demonstration of the Improvement in the Resistance to Water

Emulsions are prepared which have the following composition:

| A | Emulsifier | 3% |
|---|---|---|
|   | Diisopropyl adipate | 10% |
|   | Glycerol | 7% |
|   | Ethylhexyl methoxycinnamate | 7.50% |
|   | Octocrylene | 10% |
|   | Butylmethoxydibenzoylmethane | 2% |
| B | Acrylamide/acryloyldimethyl taurate copolymer and isohexadecane and polysorbate 80 | 1.20% |
|   | Cyclomethicone | 5% |
| C | Tetrasodium EDTA | 0.20% |
|   | Xanthan gum | 0.15% |
|   | Magnesium aluminum silicate | 0.15% |
|   | Water | q.s. for 100% |
| D | Preservative | q.s. |
|   | Tromethamine | q.s. pH = 5 |

The resistance to water is determined in vivo on a panel of volunteers according to the following protocol:

Phase 1

Determination of cutaneous regions on the back: one region per emulsion tested+one control region on which no emulsion is applied.

Application of the emulsions at the rate of 2 mg/cm$^2$.

UV irradiation over all of the regions 15 minutes after application of the emulsions (xenon lamp).

16 to 24 hours after irradiation, visual reading of the minimum erythemal doses over all of the regions (MED).

Calculation of the sun protection factors of the products tested:

$$PF \text{ product} = \frac{MED \text{ product region}}{MED \text{ control region}}$$

Phase 2

Determination of new cutaneous regions on the back: one region per emulsion tested and one control region.

Application of the emulsions at the rate of 2 mg/cm$^2$.

Bathing twice, each for 20 minutes, separated by 10 minutes.

UV irradiation over all of the regions 15 minutes after the bathing operations (xenon lamp).

Visual reading of the minimum erythemal doses over all of the regions after bathing.

Calculation of the sun protection factor after bathing $$PF \text{ product} = \frac{MED \text{ product region after bathing}}{MED \text{ control region after bathing}}$$

$$\text{Resistance to water} = \frac{\text{Sun protection factor after bathing (phase 2)}}{\text{Sun protection factor (phase 1)}}$$

The emulsions prepared are monitored by sensory evaluation.

The results are presented in table 3.

TABLE 3

| Emulsifier | Resistance to water % | Sensory evaluation: greasiness | Sensory evaluation: residue |
|---|---|---|---|
| A | 18 | 3 | 4 |
| B | 17 | 3 | 2 |
| C | 35 | 0 | 0 |
| G | 41 | 0 | 0 |

The emulsions according to the invention exhibit a significantly improved resistance to water without, however, leaving a greasy sensation or a sensation of residue on the skin.

Example 5

Demonstration of the Improvement in Foundation Emulsions

Emulsions are prepared which have the following composition:

| Fatty phase | |
|---|---|
| Emulsifier | 3% |
| Isononyl isononanoate | 10% |
| Triisostearyl citrate | 10% |
| Aqueous phase | |
| Water | q.s. for 100% |
| Iron oxides | 1.2% |
| Dimethicone PEG 7 phosphate | 0.8% |
| Titanium oxide | 12% |
| Talc | 4% |
| Butylene glycol | 4% |
| PEG 400 | 4% |
| Trishydroxyaminomethane | q.s. pH 7 |
| Polyacrylamide and $C_{13}$-$C_{14}$ isoparaffin and laureth-7 | 1.5% |

The emulsions are monitored:

By visual (macroscopic) monitoring of the stability of the emulsions with checking after 3 months of the appearance of the emulsions in the flask: smooth or granular appearance, glossy or mat appearance, monitoring of phenomena of phase separation, of release of pigments at the surface of the emulsion or of stratification of the pigments with a heterogeneous visual effect. The optimum criteria are a glossy, perfectly smooth and homogeneous emulsion without phase separation or release or stratification of the pigments and fillers. The grading is as follows: + if all the criteria are satisfactory, +/− if at least one of the criteria is unsatisfactory, 0 if none of the criteria is satisfactory.

By monitoring of the texture with the preparation, on a plexiglas sheet, of films calibrated to 120 μm and checking for the absence of agglomerates of fillers and pigments. The grading is as follows: + in the absence of specks 3 months after the manufacture of the emulsion, +/− in the presence of a few specks, 0 in the presence of numerous specks.

By an evaluation of the hold of the emulsion on the face by a professional make-up artist 4 h after application. The grading is as follows: + in the absence of migration of the pigments and fillers into the wrinkles and fine lines, +/– in the presence of moderate migration, 0 in the presence of significant migration.

By sensory evaluation: the criteria of comfort are graded from 0 to 5 by a jury of experts after application to the face. The following are evaluated: the sensation of greasiness (0=nongreasy and 5=very greasy), the sensation of freshness (0=absence of freshness and 5=significant freshness) and the ease of spreading (0=difficult to spread and 5=easy to spread).

The results are presented in table 4.

TABLE 4

| Emulsifier | A | C | D | G | H |
|---|---|---|---|---|---|
| Visual monitoring | + | + | + | + | +/– |
| Textural monitoring | +/– | + | +/– | + | +/– |
| Migration | +/– | + | 0 | + | 0 |
| Sensory evaluation: | | | | | |
| greasiness | 3 | 2 | 2 | 2 | 2 |
| freshness | 3 | 4 | 4 | 4 | 3 |
| ease of spreading | 3 | 4 | 5 | 5 | 3 |

Among the emulsifiers tested, those of the invention simultaneously provide the maximum of desired criteria.

Example 6

Demonstration of the Improvement in Foundation Emulsions at Acidic pH

Emulsions having the composition shown in example 5 are prepared at pH 5, with the emulsifiers A, G and H.

The results are presented in table 5.

TABLE 5

| Emulsifier | A | G | H |
|---|---|---|---|
| Visual monitoring | +/– | + | 0 |
| Textural monitoring | 0 | +/– | 0 |

Among the emulsifiers tested, that of the invention provides the greatest flexibility in the adjustment of the pH in an acid medium. For the other emulsifiers, the acidification of the pH brings about a totally unacceptable instability of the pigments and fillers.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. An emulsifying composition consisting of:
   a) from about 10 to about 90% by weight of alcohol, wherein said alcohol is selected from the group consisting of arachidyl alcohol, behenyl alcohol and mixtures thereof; and
   b) from about 10 to about 90% by weight of at least one phosphoric ester of said alcohol.

2. The composition according to claim 1, wherein said alcohol is from about 15 to about 90% by weight of said composition.

3. The composition according to claim 2, wherein said alcohol is from about 30 to about 70% by weight.

4. The composition according to claim 1, wherein said alcohol is a mixture of arachidyl alcohol and behenyl alcohol.

5. The composition according to claim 1, wherein said at least one phosphoric ester is from about 10% to about 85% by weight of said composition.

6. The composition according to claim 5, wherein said at least one phosphoric ester is from about 30 to about 70% by weight.

7. An emulsion comprising:
   a) from about 0.2 to about 10% by weight of the emulsifying composition according to claim 1;
   b) from about 1 to about 50% by weight of a fatty phase composed of one or more oils and/or one or more waxes; and
   c) an aqueous phase.

8. The composition according to claim 7, wherein said weight of said fatty phase is in the range of from about 5 to about 35%.

9. The composition according to claim 7, wherein said fatty phase comprises at least one component selected from the group consisting of:
   a) at least one oil; and
   b) at least one wax.

10. The composition according to claim 9, wherein said oil comprises at least one component selected from the group consisting of:
    a) vegetable oil;
    b) oils of animal origin;
    c) minerals oils;
    d) synthetic oils;
    e) fatty acids; and
    f) fatty alcohols.

11. The composition according to claim 9, wherein said wax comprises at least one component selected from the group consisting of:
    a) fatty substances;
    b) beeswax;
    c) carnauba wax;
    d) candelilla wax;
    e) ouricury wax;
    f) Japan wax;
    g) cork fiber;
    h) sugarcane wax;
    i) paraffin waxes;
    j) lignite waxes;
    k) microcrystalline waxes;
    l) lanolin wax;
    m) ozokerite;
    n) polyethylene wax;
    o) hydrogenated oils;
    p) silicone waxes;
    q) vegetable waxes;
    r) fatty alcohols;
    s) fatty acids; and
    t) glycerides.

12. The composition according to claim 7, wherein said composition further comprises from about 10% by weight of a stabilizing agent.

13. The composition according to claim 12, wherein said stabilizing agent comprises at least one component selected from the group consisting of:
    a) magnesium silicate;
    b) aluminum silicate;
    c) sodium silicate;
    d) zanthan gum;

e) acacia gum;
i) locust bean gum;
g) scleroglucan gum;
h) gellan gum;
i) alginates;
j) cellulose and its derivatives;
k) clays;
l) starches and its derivatives;
m) acrylic acid polymers;
n) copolymers;
o) acryloyldimethyl taurate polymers;
p) polyvinylpyrrolidone;
q) acrylamide polymers; and
r) polyurethanes.

14. The composition according to claim 7, wherein said composition further comprises from up to about 10% by weight of at least one additive.

15. The composition according to claim 14, wherein said additive comprises at least one component selected from the group consisting of:
    a) coemulsifiers;
    b) dispersants;
    c) fragrances;
    d) preservatives; and
    e) DHA.

16. The composition according to claim 7, wherein said composition further comprises from about 0.5 to about 50% by weight of at least one component selected from the group consisting of:
    a) organic pigments;
    b) inorganic pigments; and
    c) fillers.

17. The composition according to claim 16, wherein said weight of said components is in the range of from about 2 to about 35%.

18. The composition according to claim 7, wherein said composition further comprises up to about 20% by weight of at least one cosolvent selected from the group consisting of:
    a) glycerol;
    b) sorbitol;
    c) PEG;
    d) monopropylene glycol;
    e) butylene glycol;
    f) isoprene glycol;
    g) 2methyl-1, 3-propanediol;
    h) ethanol; and
    i) hexylene glycol.

19. The composition according to claim 18, wherein said weight of said cosolvent is up to about 10%.

20. The composition according to claim 7, wherein said emulsion further comprises:
    a) from about 1 to about 40% by weight at least one organic or inorganic sunscreen; and
    b) up to about 30% by weight of a water-resisting agent.

21. The composition according to claim 20, wherein said composition is an antisun emulsion.

22. The composition according to claim 20, wherein said sunscreen comprises from about 1 to about 20% by weight of the total emulsion.

23. The composition according to claim 20, wherein said water-resisting agent comprises about 10% by weight of the total emulsion.

24. The composition according to claim 7, wherein said composition comprises:
    a) from about 0.2 to about 10% by weight of said emulsifying composition;
    b) from about 0 to about 10% by weight of a coemulsifier;
    c) from about 1 to about 50% by weight of a fatty phase; and
    d) from about 0 to about 10% by weight of a stabilizing agent.

25. The composition according to claim 24, wherein the weight of said fatty phase is in the range of from about 5 to about 35%.

26. The composition according to claim 25, wherein said weight is in the range of from about 5 to about 25%.

27. The composition according to claim 7, wherein said emulsion is a makeup emulsion.

28. The composition according to claim 16, wherein said composition has a pH in the range of about 5 to about 6.

29. An emulsifying composition consisting of:
    from about 10 to about 90% by weight of a mixture of arachidyl alcohol and behenyl alcohol; and
    from about 10 to about 90% by weight of a mixture of phosphoric esters of arachidyl alcohol and phosphoric esters of behenyl alcohol.

* * * * *